(12) United States Patent
Breivik et al.

(10) Patent No.: US 8,383,178 B2
(45) Date of Patent: Feb. 26, 2013

(54) STABILISATION OF PIGMENTS AND POLYUNSATURATED OILS AND OIL CONCENTRATES

(75) Inventors: Harald Breivik, Porsgrunn (NO); Lola Irene Sanna, Porsgrunn (NO); Berit Annie Aanesen, Skien (NO)

(73) Assignee: Pronova Biopharma Norge AS, Baerum (NO)

( * ) Notice: Subject to any disclaimer, the term of this patent is extended or adjusted under 35 U.S.C. 154(b) by 1037 days.

(21) Appl. No.: 10/168,565

(22) PCT Filed: Dec. 20, 2000

(86) PCT No.: PCT/NO00/00439
§ 371 (c)(1),
(2), (4) Date: Nov. 7, 2002

(87) PCT Pub. No.: WO01/46355
PCT Pub. Date: Jun. 28, 2001

(65) Prior Publication Data
US 2003/0144355 A1    Jul. 31, 2003

(30) Foreign Application Priority Data
Dec. 22, 1999  (NO) .................................. 19996411

(51) Int. Cl.
*A21D 4/00* (2006.01)
*A23B 7/154* (2006.01)
*A23C 3/00* (2006.01)
*A23K 3/00* (2006.01)
*A23L 3/34* (2006.01)
*C12H 1/10* (2006.01)

(52) U.S. Cl. ..................................................... 426/321

(58) Field of Classification Search ................. None
See application file for complete search history.

(56) References Cited

U.S. PATENT DOCUMENTS

| | | | | |
|---|---|---|---|---|
| 2,875,218 A | * | 2/1959 | Dazzi ............................ | 564/152 |
| 3,288,794 A | * | 11/1966 | Kuceski ........................ | 544/386 |
| 6,235,913 B1 | * | 5/2001 | Raths et al. .................... | 554/98 |

FOREIGN PATENT DOCUMENTS

| | | |
|---|---|---|
| EP | 0574974 | 12/1993 |
| WO | 8703899 | 7/1987 |
| WO | 9612415 | 5/1996 |
| WO | WO 99/10319 A1 * | 3/1999 |
| WO | 0001249 | 1/2000 |

OTHER PUBLICATIONS

Urdahl et al. Water-in-crude oil emulsions from the Norwegian Continental Shelf. A stabilization and destabilization study. Journal of Dispersion Science and Technology (1995), 16(7), 557-74.*
ScienceLab.com. "Material Safety Data Sheet: Hexylamine" (2005). [Retrieved on Feb. 15, 2008]. Retrieved from the Internet:<URL www.sciencelab.com/msds.php?msdsld=9924260>.*
Merriam-Webster Dictionary [Online]. "Concentrate". [Retrieved Aug. 27, 2010]. Retrieved from the Internet: <URL: http://www.m-w.com/dictionary/concentrate>.*
"Dimethylamine" The Merck Index (Twelfth Edition). Monograph 3278. Merck & Co. Inc. p. 547.*
Merriam-Webster Dictionary [Online]. "Aqueous". [Retrieved Mar. 8, 2012]. Retrieved from the Internet: <URL: http://www.m-w.com/dictionary/aqueous>.*
Kaushik, S.J., et al. "Utilization of Dietary Urea in Rainbow Trout", Annals of nutrition & metabolism, vol. 27 (1983), pp. 94-106.
WPI/Derwent's abstract, Accession No. 1994-014007, week 9402, Abstract of KR, 9305193 (Kim D. et al.), Jun. 16, 1993.

* cited by examiner

*Primary Examiner* — Leslie A. Royds Draper
(74) *Attorney, Agent, or Firm* — Wenderoth, Lind & Ponack, L.L.P.

(57) ABSTRACT

The present invention relates to a method for stabilizing vegetable, marine and single cell oils/oil concentrates as well as pigments like astaxanthin and canthaxanthin with regard to oxidation. It also relates to a feed for salmonids, and a method for optimising the effect of the pigment in feed for salmonids. Furthermore, the invention relates to a health care product and a composition for prophylaxis or therapeutical treatment. Essential features by the invention are treatment by or presence of amines/amides.

3 Claims, 8 Drawing Sheets

Fig. 4a: Weight-gain measurement of IP of oil samples

Fig. 5:

Fig. 5a: POV, p-AV and IP of treated oils

*) The IP value for A3 is a minimum value

Fig. 6

STABILISATION OF PIGMENTS AND POLYUNSATURATED OILS AND OIL CONCENTRATES

This invention relates to a method for stabilising vegetable oils, marine oils and single cell oils, oil concentrates as well as pigments like astaxanthin and canthaxanthin. It also relates to a feed for salmonids, and a method for optimising the effect of the pigment in feed for salmonids, and furthermore to a health care product and a composition for prophylaxis or therapeutical treatment.

A problem for the aquaculture industry is degradation and low quality of the fat components in the feed due to oxidation. When marine fat, which is the main fat source in fish feed, reacts with oxygen, firstly primary oxidation products like peroxides are formed. These are measured as the peroxide value (POV). Peroxides from polyunsaturated fat are unstable and easily degraded by transformation to secondary oxidation products.

Secondary oxidation products are a complex group of compounds like aldehydes and ketones. To analyse the amount of secondary oxidation products the anisidine value is measured. The anisidine number is the intensity of a colour that develops during reaction between the chemical anisidine and aldehydes in the fat. The anisidine value is given without denomination.

The level of oxidation is often given as totox-value. The Totox-value is defined as two times the peroxide value added with the anisidine value.

For fish feed an oil having a totox-value below 20 should be used to secure optimal growth for the fish. It is today difficult to provide oils having a totox-value below 20. Oils with a totox-value of up to 30 are available. By reducing the oxidation oils not nutritional acceptable could be made available as a source for fat in feed. This would be very much appreciated by the aquaculture industry as the supply of fish oils are limited.

The oxidative stability of oils can be compared by accelerated tests, such as the weight-gain method, where oil samples are stored at elevated temperatures and oxygen atmosphere. The weight increase due to oxygen absorption is measured and plotted against time. At a certain time, depending on the oils resistance to oxidation, weight increase will be rapid, and the time before this happens is noted as the oils induction time (IP).

Oxidation of fat is a problem also with regard to fat sources like vegetable oils and animal oils other than marine oils as well as single cell oils.

Furthermore, for the aquaculture industry it has been an economic problem that farmed fish like salmon and trout do not naturally achieve the same strongly red colour as the wild species. Such farmed fish are palely red, if not large amounts of red pigments are artificially supplied, and therefore not as attractive as the wild fish to the customer.

Today pigments like astaxanthin and canthaxanthin are added to the fish feed to make the fish meat more red.

Commercially available astaxanthin products are very expensive and their biological retention is very low (typically 10-12%). In addition astaxanthin is a rather unstable compound, which of course is a drawback. The low stability of astaxanthin is due to oxidation. Commercial pigment products are formulated in order to avoid or reduce oxidation. One typical formulation for astaxanthin is with gelatine and starch. The formulations used are often, however, not optimal with respect to biological availability of the pigment, and a new formulation, combining a high degree of stability with improved biological availability would be of great economical benefit to the aquaculture industry. A more stable pigment is thus highly desired as this would give possibilities for making a formulation more optimal with regard to biological entrance and consequently possibilities for considerably economic saving.

It has surprisingly been found that by treating fish oils with certain amines/amides, oxidation has been considerably reduced. Even more surprisingly it was notified that oxidation of astaxanthin kept in a fish oil treated by amines/amides was considerably reduced.

Marine oils, i.e. cod-liver oil and oils from fish rich in omega-3 acids are being marketed because of their beneficial effects to health. There are international regulations that states maximum oxidation levels of such products (example: European Pharmacopoeia monograph 1998:1192 and 1193 for cod-liver oil). The present invention can be utilised in order to reduce the levels of oxidation products in such oils.

Concentrates of polyunsaturated fatty acids, especially concentrates of omega-3 fatty acids, are marketed as health care products, and also registered as medical products. The medical products might be useful in treatment and prophylaxis of hyperlipemiae and therewith correlated pathologies, thromboses, platelet agglutination, cardiac infarction, hypertension, anticoagulants, prevention of atherosclerosis, cerebral infarction, lesion and occlusions caused by vasomotor spasms, diabetes and its complications, acute and chronic inflammations, self-immune syndromes, preventing the side effects at gastroenteric level of non-steroid anti-inflammatory agents, tumour prevention, IgA-nephropathy and pregnancy induced hypertension.

These products are very labile to oxidation. It has now surprisingly been found that by treating such concentrates with amines/amides, oxidation has been considerably reduced.

The main object of the invention is to provide a method for stabilising vegetable oils, marine oils and single cell oils as well as concentrates of such oils with regard to oxidation.

Another main object of the invention is to provide a method for stabilising pigments like astaxanthin and canthaxanthin, with regard to oxidation.

Further, it is an object of the invention to provide a feed for salmonids being improved with regard to storage stability/degradation and biological effect of the pigment.

Still another object of the invention is to provide a method for optimising the effect of the pigment in feed for salmonids.

Another object of the invention is to provide a health care and pharmaceutical product comprising oil concentrates having reduced levels of oxidation.

These and other objects are obtained by treatment or presence of amines/amides as defined in the accompanying claims.

A preferred feature by this invention is that the oil is treated with amines/amides and added to the fodder before or after extrusion. The oil is treated either by heating in the presence of amines/amides, or by reacting with an aqueous mixture of amines/amides. Another preferred feature is that amines are added directly to the fodder mixture, either in an aqueous phase or in solid form.

In the following the invention will be further explained by examples and attached illustrations FIGS. 1-6. The examples are just meant to be illustrative and shall not be considered as limiting.

Concentrates of polyunsaturated fatty acids are produced in a number of ways, as glycerides, as esters or free fatty acids or salts to give some possibilities. It is obvious for the person known in the art that the present invention is not limited to the concentrates that have been used in the examples. The examples are just illustrations, the invention could be beneficial for any of these concentrates, especially concentrates of omega-3 acids. It will also be obvious to the person known in the art that treatment does not have to be performed with the finished product, beneficial effects will be obtained also if the level of oxidation products is reduced at an earlier step during production. It may also be possible to add production steps in order to remove residual amounts of amines/amides from the finished products.

TABLE 1

Experimental design for examples 1–3.

| Code | Substance | Amount per 95 g fish oil | Melting (boiling) point (° C.) | Heating temperature (° C.) |
|---|---|---|---|---|
| A0 | No (control) | — | — | 90 |
| A2 | Allylurea | 0.083 moles | 84 | 90 |
| A3 | Hexylamine | 0.083 moles | −23 bp 131 | 90 |
| A4 | N-ethyldiiso-propylamine | 0.083 moles | <−50 (bp 127) | 90 |
| B0 | No (control) | — | — | 140 |
| B2 | Allylurea | 0.083 moles | 84 | 140 |
| B4 | N,N'-dimethylurea | 0.083 moles | 102 | 140 |
| B5 | Oxamide | 0.083 moles | 300 | 140 |
| B7 | Butyramide | 0.083 moles | 114 (bp 216) | 140 |
| C0 | No (control) | — | — | — |

It is obvious for a person known in the art that many or all of the substances in table 1 will act in a similar way. Other amines/amides will also give similar results. Other concentrations of amines or amides would also give similar effects.

EXAMPLE 1

0.083 moles of amine/amide was added to 95 g of a fish oil, which was progressively heated to 90° C. (A series) or 140° C. (B series) during agitation to dissolve the substances in the oil. Melting points, and boiling points where relevant, of the substances, are given in table 1. After 30 minutes at this temperature, the oil was cooled and filtered.

The fish oil was analysed with respect to peroxide value (POV) and p-anisidine value (p-AV) before the experiments, and the Totox value was calculated (Totox=2×POV+p-AV).

During treatment, samples were taken when the oil reached the chosen temperature (t=0) and after 30 minutes (t=30). The samples were filtered and analysed regarding POV and p-AV.

The peroxide value is the number that expresses in milliequivalents of active oxygen the quantity of peroxide contained in 1000 g of the substance as determined by the method Ph. Eur. V. 3.4.5.

The p-anisidine value is related to the intensity of the colour that is formed by chemical reactions between p-anisidine and carbonyl compounds (i.e. aldehydes) in the oil. The analytical procedure as given by the European Pharmacopoeia in the monograph for Cod-liver oil (type A) (monograph 1998:1192) was used.

Before treatment, the fish oil had the following analytical values: POV=2.5 meq/kg, p-AV=21.2, Totox=26.2.

Figure 1:
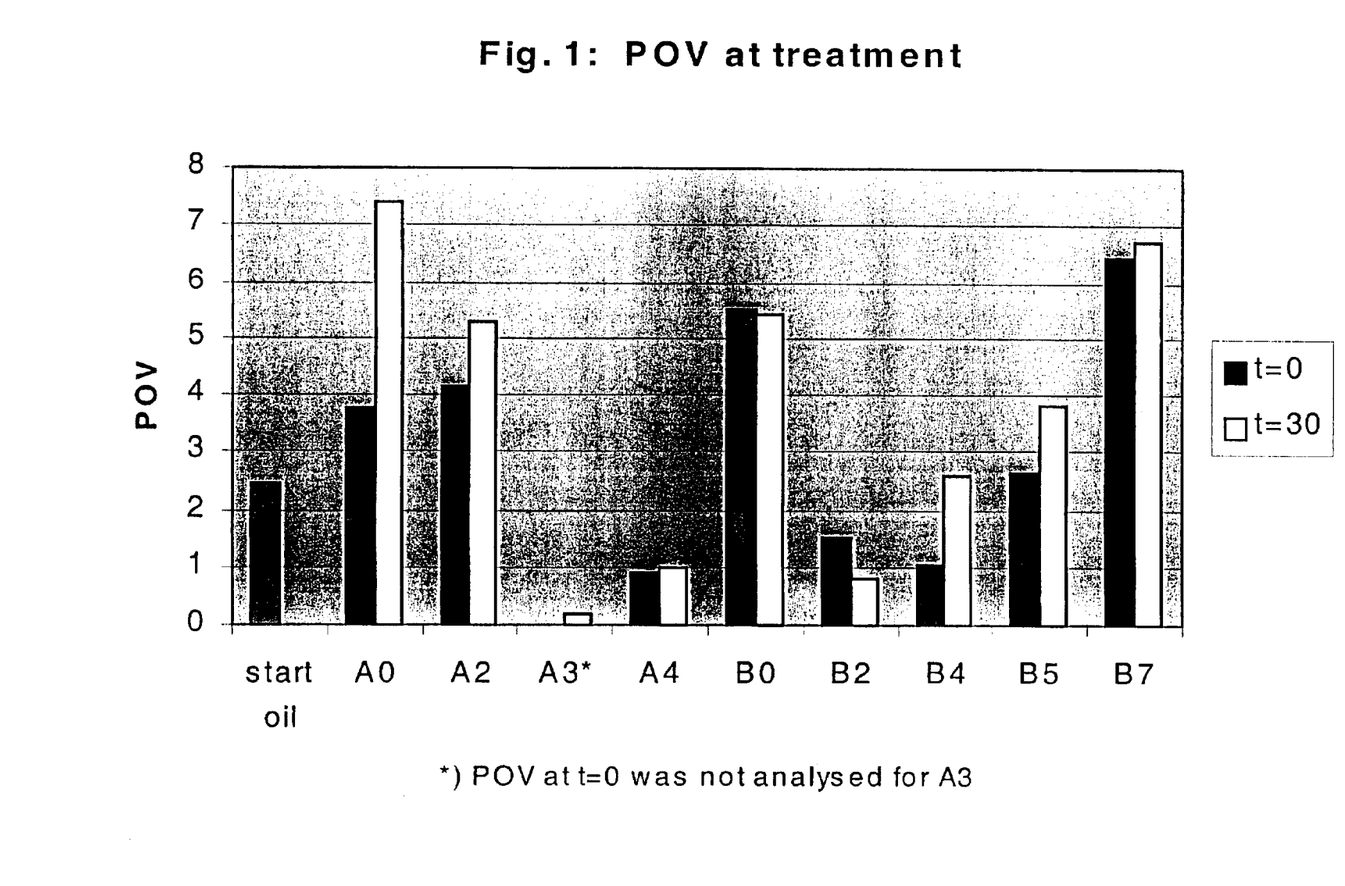
FIG. 1 shows a diagram concerning levels of primary oxidation products, before, during and after treatment of a fish oil with and without amines/amides.
Figure 2:
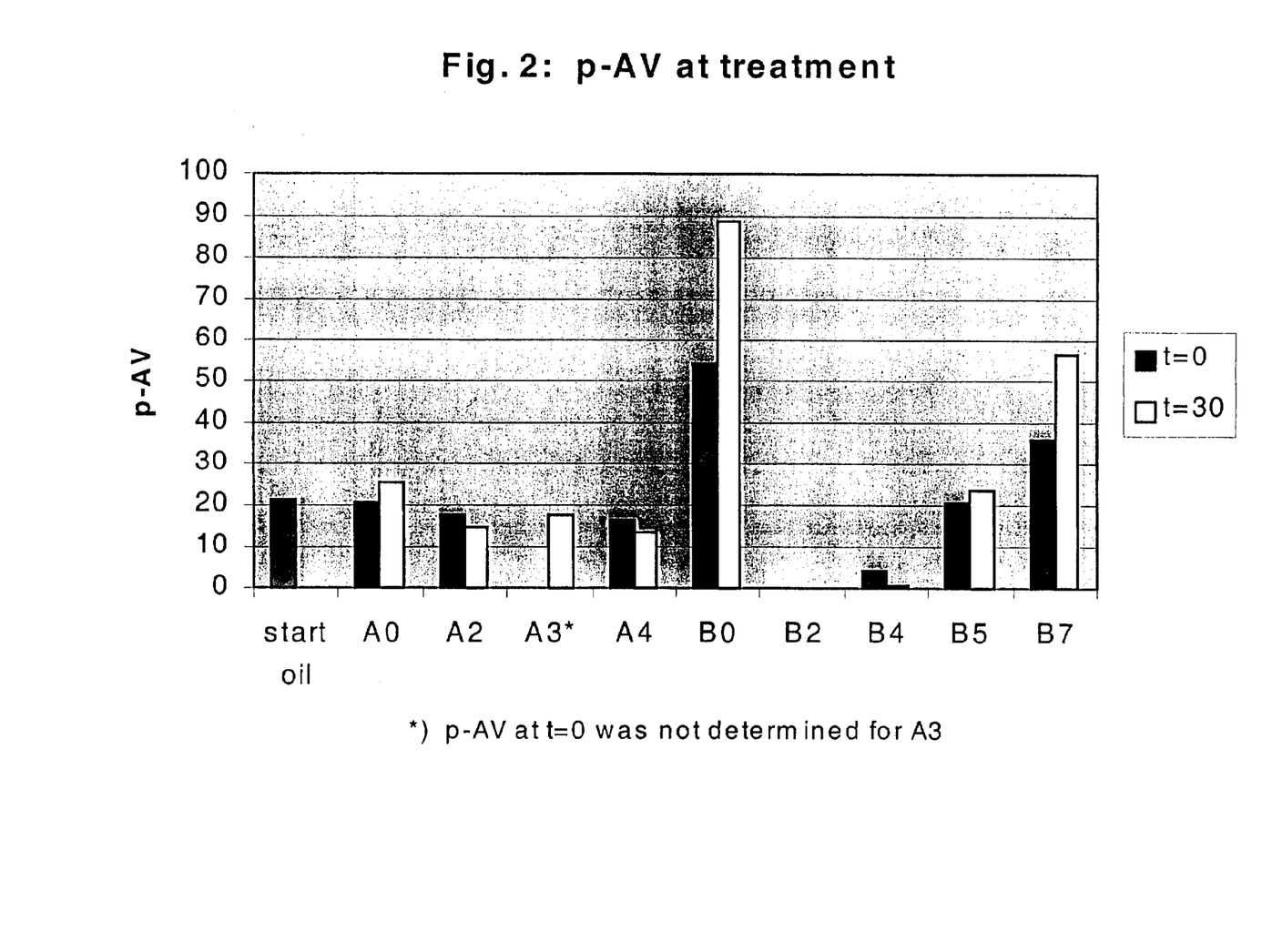
FIG. 2 shows a diagram concerning oxidation with regard to secondary oxidation products, before, during and after treatment of a fish oil with and without amines/amides.
Figure 3:
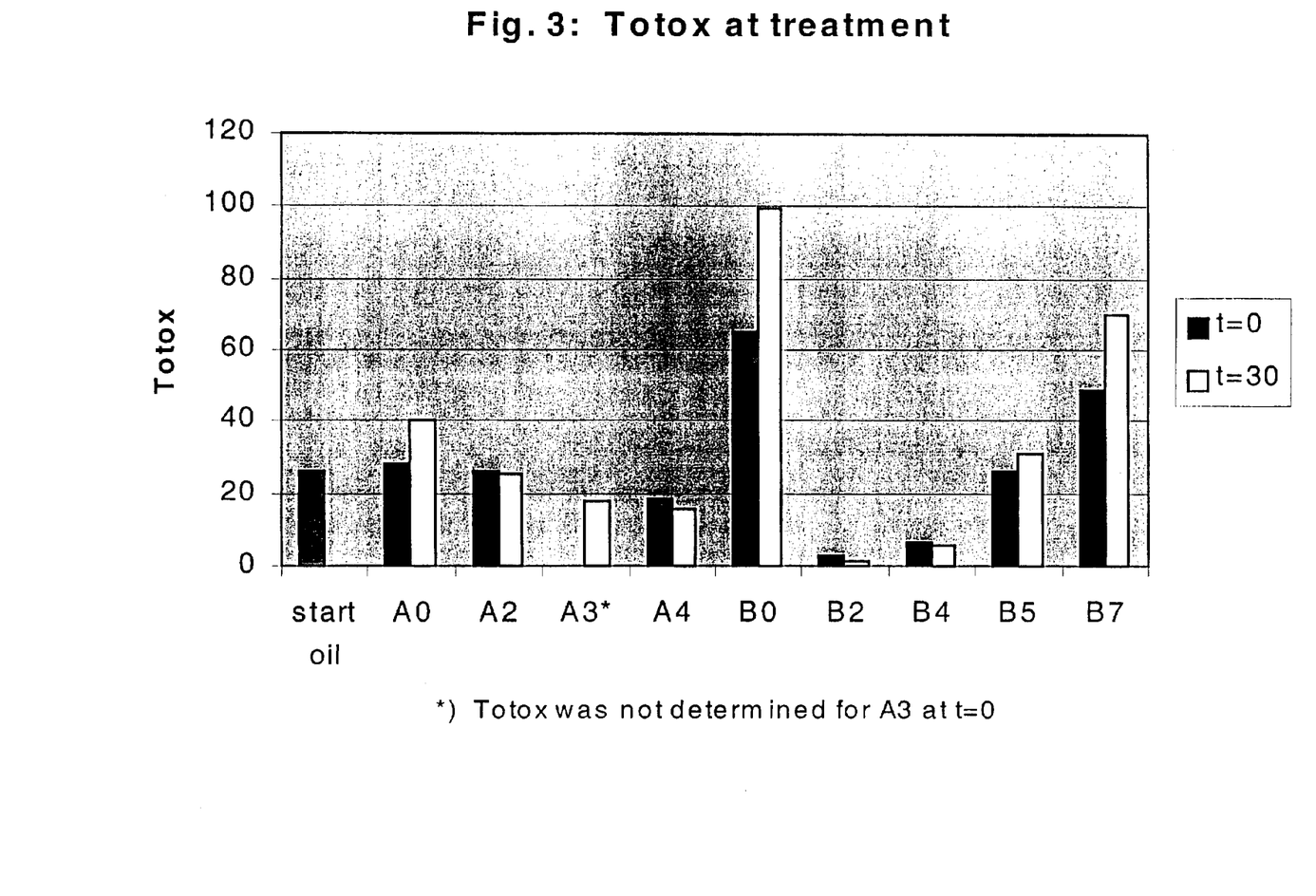
FIG. 3 shows a diagram concerning primary and secondary oxidation in a fish oil treated with amines/amides, in comparison with untreated fish oil.
Figure 5:
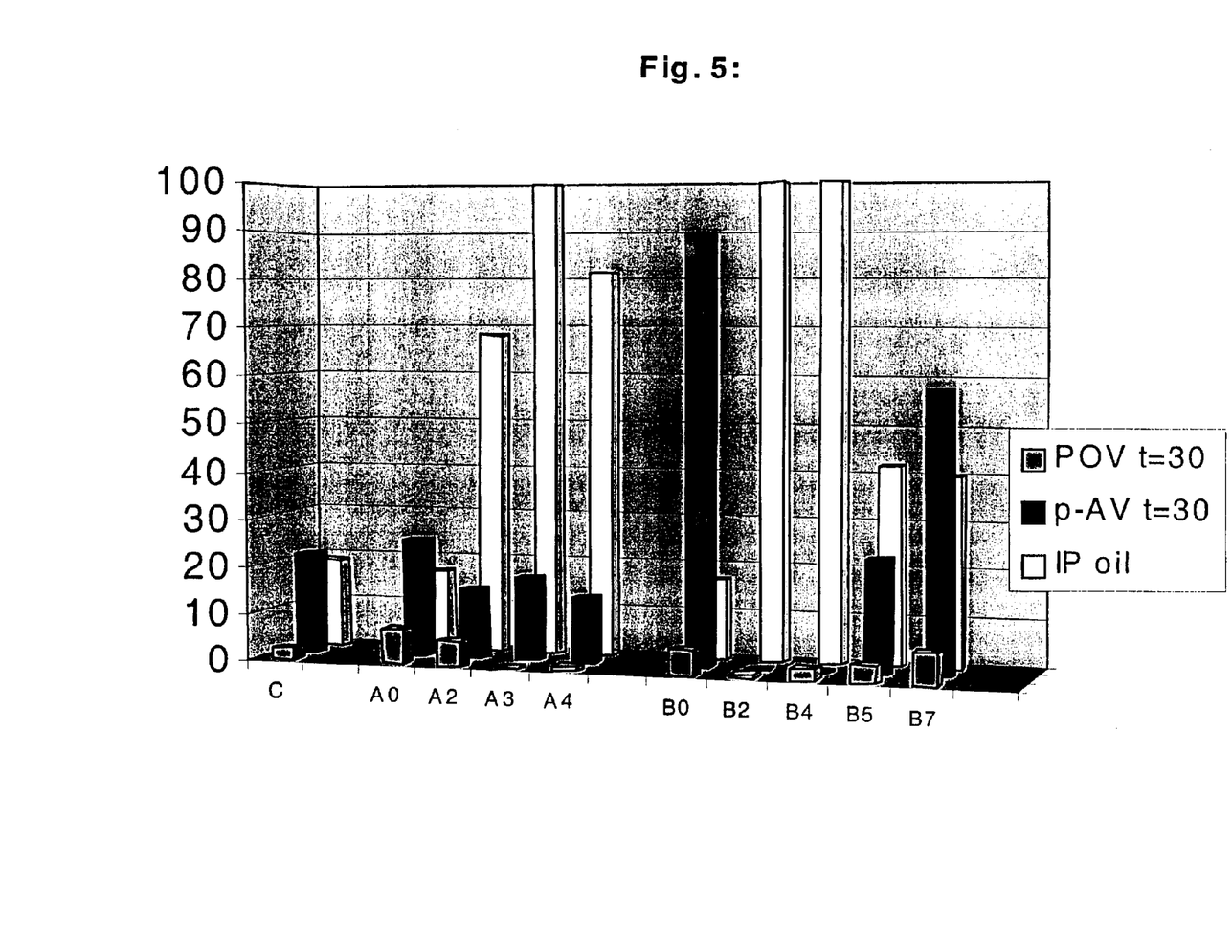
FIGS. 5 and 5$a$ shows another diagram concerning oxidation in a fish oil treated with amines/amides, in comparison with untreated fish oil.

Values during and after the treatments are given in FIGS. 1 (POV), 2 (p-AV) and 3 (Totox), as well as in FIG. 5. It can be seen that the treatments significantly reduced POV and p-AV values.

EXAMPLE 2

Three 3-g samples of filtered untreated oil, and three 3-g samples of filtered oil from each of the treatments described in table 1, were placed in identical petri dishes (60 mm, with loose fitting lids) and accurately weighed. The petri dishes were placed in an oven at about 35° C., and the weight increase related to oxygen uptake (oxidation) was recorded by weighing 3 times/week.

Figure 4:
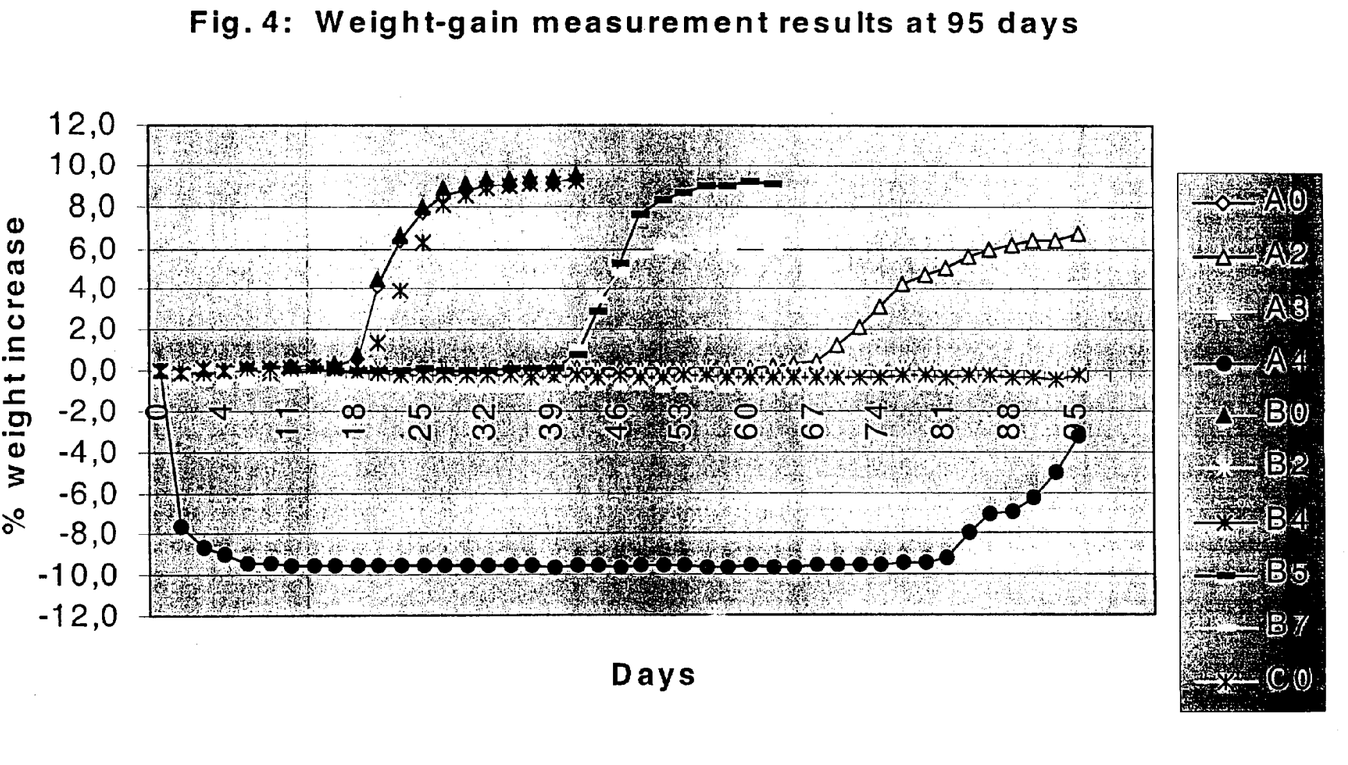
FIGS. 4 and 4$a$ shows a diagram concerning oxidation in a fish oil treated with amines/amides, in comparison with untreated fish oil.

The results given in FIG. 4 and in FIG. 5 indicates large differences in stability as measured by induction periods (IP; i.e. the time before rapid oxygen uptake), ranging from 17 days (oils heated to 90° C. or 140° C. without any substance added) and 19 days (untreated oil), to 95 days (oils treated with hexylamine at 90° C., or allylurea at 140° C., or N,N'-dimethylurea at 140° C.).

Figure 4A:
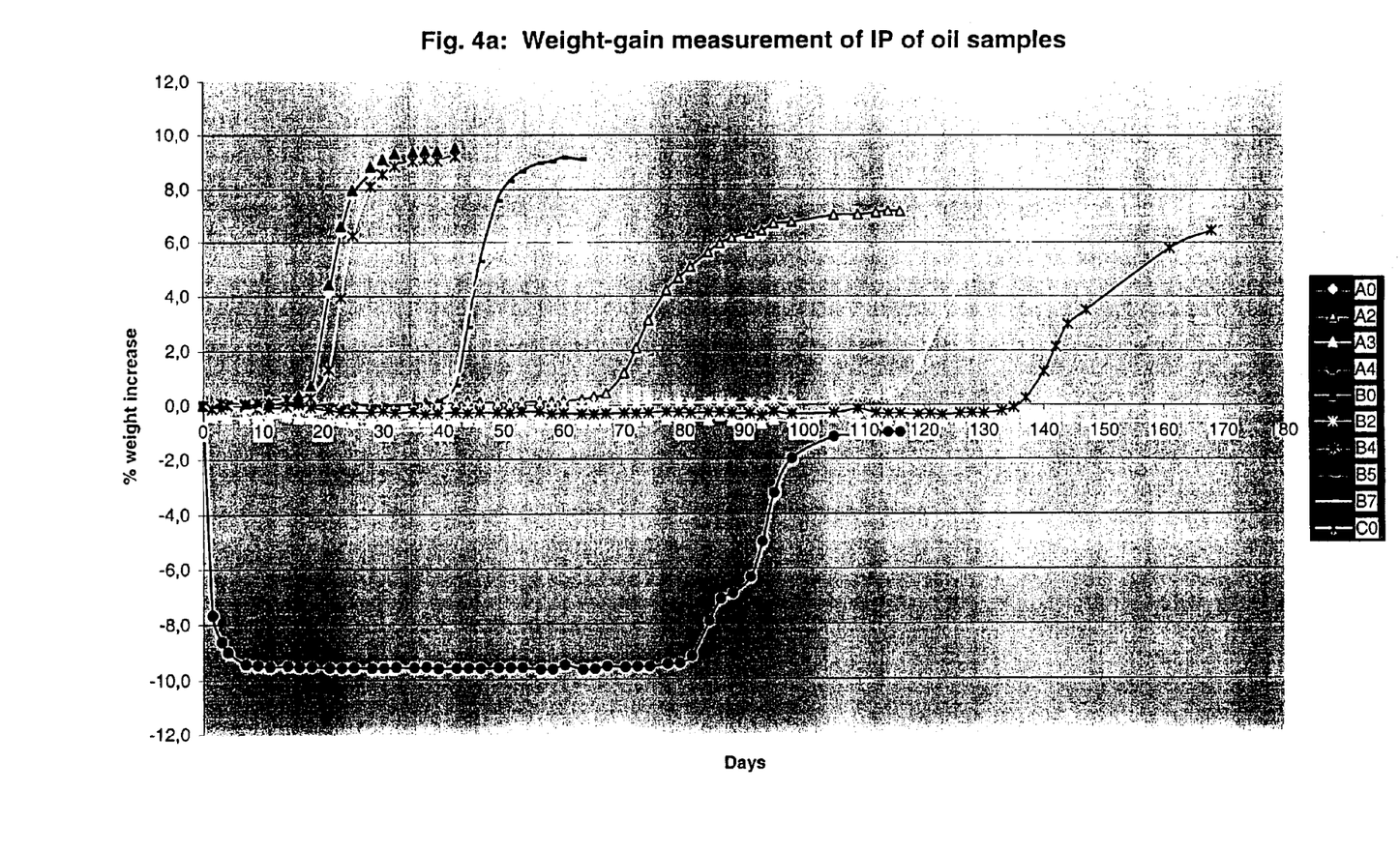
Figure 5A:
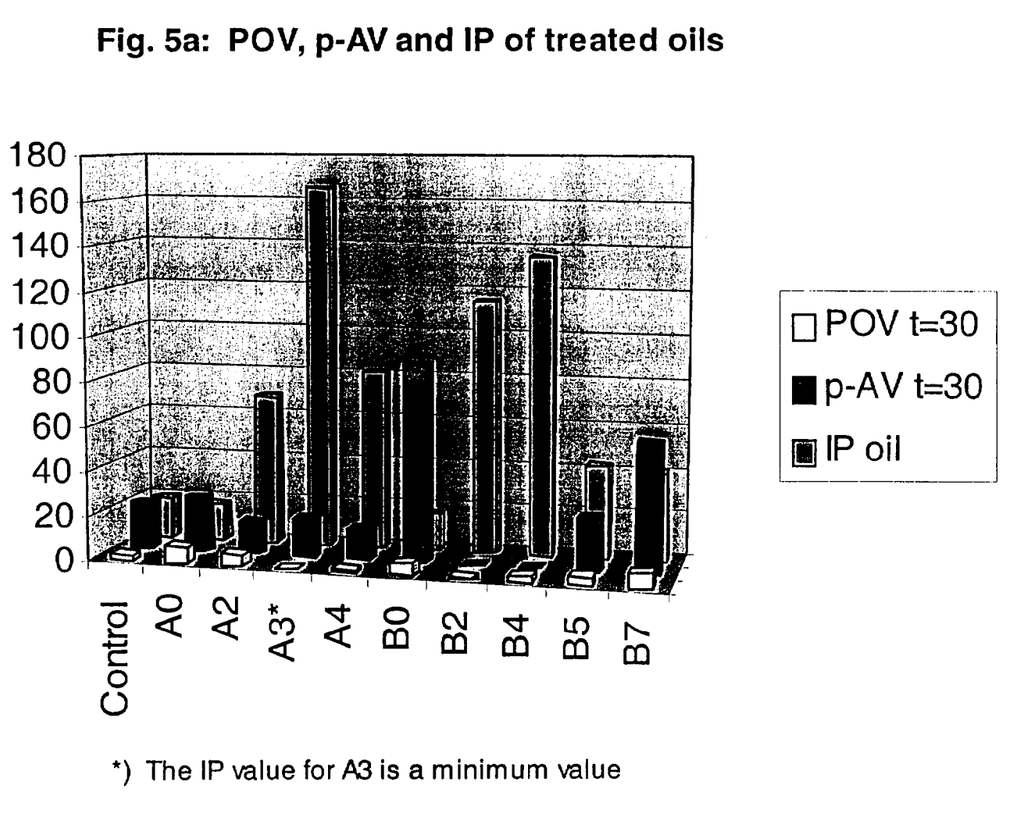
Figure 6:
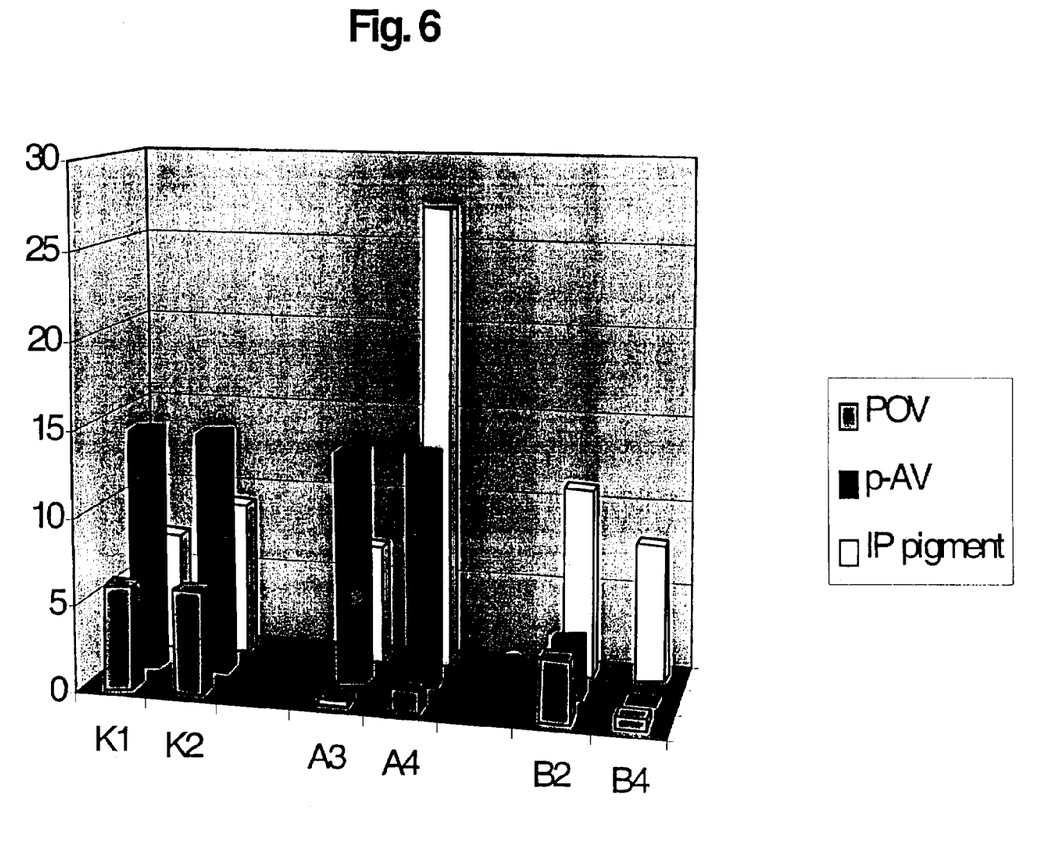
FIG. 6 shows a diagram concerning pigment stability in a fish oil treated with amines/amides, in comparison with pigment stability in untreated fish oil.

The experiment was continued for another 70 days, resulting in that the samples of oil B4 (treated with N,N'-dimethylurea at 140° C.) showed a rapid weight increase at day 135, while the samples of oil A3 (treated with hexylamine at 90° C.) still were stable. Results from the prolonged storage are given in FIGS. 4$a$ and 5$a$.

EXAMPLE 3

Portions of fish oil were treated with amines/amides (0.083 moles per 95 g oil) at elevated temperatures for 30 minutes as described in example 1, and were cooled and filtered. Samples were then taken for the analysis of POV and p-AV. From each oil, 3×100 g were transferred to three 250 ml reaction flasks.

To two of the samples from each oil, 80 ppm astaxanthin was added as a chloroform solution. The last 100 g sample was used as a background correction at later analyses.

In addition, two 100 g samples of untreated oils were transferred to 250 ml reaction flasks, and 80 ppm astaxanthin was added to each of them as above. These were used as controls.

Ultrasound treatment was used to mix astaxanthin into the oils. The reaction flasks were then placed in a heating/shaking bath at 80° C., and a continuous flow of air was directed through each sample. Analytical samples were taken regularly, and the UV absorbance of these were measured at the observed $\lambda_{max}$ for astaxanthin in each particular oil type. Absorbances were corrected for background absorption caused by the oil.

As astaxanthin is oxidised, the absorbance is diminished. From each curve, the time before all of the added astaxanthin is consumed (IP pigment) is estimated, and these results are displayed in FIG. 6.

It was observed that the pigment degradation was significantly delayed in some of the samples, as compared with pigment degradation in untreated fish oil.

By addition of conventional antioxidants like tocopherol, ascorbic acid and derivatives of ascorbic acid to the oils, oil concentrates or pigments the oxidation is reduced even more than by only treating with amines/amides. Thus, treatment with amines/amides and possible other antioxidants is also included in the scope of the present invention.

Amines/amides may be added in a number of ways and not only directly to an oil/oil concentrate as described in the examples above. At production of a feed the amines/amides can be added for instance during the extruding, by vacuum coating, spray coating and by oil bath. The amines/amides can also be added in the water phase or in solid form.

According to the invention 1-200 g amines/amides is added per kg oil/oil concentrate. Preferably, 1-120 g amines/amides is added, and more preferably 0.1-50 g amines/amides is added.

The meal which is an important ingredient in the feed is of marine or vegetable origin. Fish meal, which typically contains around 10% fat, is commonly used in fish feed. The fat from the fish meal is however strongly oxidised. Thus, it would be favourable to add oil treated by amines/amides according to this invention to the meal before the pigment is brought into the feed mixture.

As amines/amides generally have a low solubility in oils at ambient temperature, it will be possible to remove most of the amines/amides by cooling and separating (the amines/amides) from the oil before it is utilised in feed production. The amines/amides are generally much more soluble in water than in oil, thus letting the oil react with amines/amides in aqueous solution will allow very little amines/amides to enter into the oil phase. Accordingly, it is possible to ensure that very small amounts of amines/amides will be present in the feed product.

By removal as described above, the amine/amide content of a processed oil will typically be in the order of 0.01-2 g/kg. As an example, the solubility of urea at ambient temperature is at approx. 1 g per kg oil. By treating the oil with amine/amide dissolved in water, the residual amount in the oil phase will be much lower than this upper solubility limit.

Besides reducing the oxidation and thus improving the quality of the fat and pigments during the production process, this invention will involve prolonged storing time for the feed. Stability of the pigment with regard to oxidation is a factor that decides for how long time the feed can be stored. A pigment having an improved stability gives a feed having an increased storing time. This gives the advantage that larger stocks may be built. In that way feed producing industries will be less vulnerable with regard to for instance production stop.

Thus, according to the present invention it has been demonstrated that oils and oil concentrates treated by amines/amides and pigments which have stayed in contact with oils or oil concentrates treated by amines/amides are less exposed to oxidation and thereby degradation than untreated oils and pigments not being in contact with amine/amide-treated oils. Furthermore, this invention discloses a feed having ability for being stored longer than any other similar known feed, and also a feed where the effect of the pigments are higher than in any previous known feed.

The invention claimed is:

1. A method of reducing the anisidine value of a vegetable oil, a marine oil comprising omega-3 fatty acid, a single cell oil, or a concentrate thereof, having an anisidine value, comprising:
    reacting the oil or oil concentrate with an aqueous mixture of 0.1-120 g of one or more amines or amides per kg oil or oil concentrate under heat at a temperature above the melting point of the one or more amines or amides, to allow the oil or oil concentrate to react with the one or more amines or amides in aqueous solution to lower the anisidine value of the oil or oil concentrate; and
    wherein the one or more amines or amides are selected from the group consisting of allylurea, N-ethyldiisopropylamine, N,N'-dimethylurea, oxamide and butyramide.

2. The method according to claim 1, wherein the oil or oil concentrate is heated for 20-30 minutes.

3. The method according to claim 2, wherein the temperature of the heating is 90° C. or 140° C.

* * * * *